United States Patent
Yamamoto et al.

(10) Patent No.: US 6,698,291 B2
(45) Date of Patent: Mar. 2, 2004

(54) ULTRASONIC INSPECTION APPARATUS

(75) Inventors: Noboru Yamamoto, Tsuchiura (JP); Ken Takeuchi, Ibaraki (JP); Naoya Kawakami, Tsuchiura (JP); Toshiyuki Hebaru, Tsuchiura (JP); Makoto Ishijima, Ibaraki (JP); Tohru Miyata, Tsuchiura (JP)

(73) Assignee: Hitachi Kenki FineTech. Co., Ltd., Tokyo (JP)

( * ) Notice: Subject to any disclaimer, the term of this patent is extended or adjusted under 35 U.S.C. 154(b) by 0 days.

(21) Appl. No.: 10/382,937

(22) Filed: Mar. 7, 2003

(65) Prior Publication Data

US 2003/0167849 A1 Sep. 11, 2003

(30) Foreign Application Priority Data

Mar. 11, 2002 (JP) .......................... 2002-065909

(51) Int. Cl.$^7$ ............................ G01N 29/04; G11C 8/00
(52) U.S. Cl. ............................ 73/620; 73/633; 73/626; 365/230.04; 365/194; 365/239; 600/443; 600/444; 600/447
(58) Field of Search ........................ 73/602, 620, 625, 73/627, 628, 629, 633, 621, 624; 600/407, 437, 443, 444, 447; 365/230.02, 230.03, 230.04, 189.01, 189.04, 239

(56) References Cited

U.S. PATENT DOCUMENTS

| | | | | |
|---|---|---|---|---|
| 4,398,540 A | * | 8/1983 | Takemura et al. .......... 600/441 |
| 4,959,998 A | * | 10/1990 | Yano ........................... 73/626 |
| 5,337,289 A | * | 8/1994 | Fasching et al. ............ 367/140 |
| 6,314,046 B1 | * | 11/2001 | Kamiya et al. ........ 365/230.04 |

* cited by examiner

*Primary Examiner*—Hezron Williams
*Assistant Examiner*—Rose M. Miller
(74) *Attorney, Agent, or Firm*—Mattingly, Stanger & Malur, P.C.

(57) ABSTRACT

An ultrasonic inspection apparatus obtains information on the interface of a sample as digital waveform data for any "unit measurement range" and is provided with at least two data memories and controlled by a scan state monitoring signal showing the scan state of a unit measurement range belonging to a first group or a unit measurement range belonging to a second group. A comparator-register/memory-control-circuit outputs the scan state monitoring signal to the two data memories. The operating states of the two data memories being controlled by the scan state monitoring signal to alternate between writing of digital waveform data and readout of digital waveform data.

5 Claims, 4 Drawing Sheets

FIG. 4 ial analog-type ultrasonic inspection apparatus will be explained first referring to FIG. 3. A

ULTRASONIC INSPECTION APPARATUS

BACKGROUND OF THE INVENTION

1. Field of the Invention

The present invention relates to an ultrasonic inspection apparatus, and more particularly, relates to a digital type ultrasonic inspection apparatus reducing the dead time in the scan operation of a scanner to zero by utilizing large-volume data transfer.

2. Description of the Related Art

A conventional general analog-type ultrasonic inspection apparatus will be explained first referring to FIG. 3. A sample or an inspected object 101 is placed in the water of a water tank 102. The water tank 102 is placed on a measurement stage 103. A scanner 104 is placed on the water tank 102. The scanner 104 is attached to the measurement stage 103. The scanner 104 is comprised of an X-axis scanner 105, Y-axis scanner 106 and Z-axis scanner 107. The Z-axis scanner 107 is provided at its bottom with an ultrasonic probe 108. The tip of the ultrasonic probe 108 faces the sample 101 at the bottom side. The X-axis, Y-axis and Z-axis as axes of the scan operation of the scanner 104 are perpendicular to each other. The operations of the X-axis scanner 105, Y-axis scanner 106 and Z-axis scanner 107 are controlled by a motor controller 109. Under the control of the motor controller 109, the scanner 104 independently scans along the X-axis, Y-axis and Z-axis. The motors of the scanner 104 for the three axes have encoders 110 respectively. The encoders 110 for the X-axis, Y-axis and Z-axis output trigger signals indicating the positional coordinates on the X-axis, Y-axis, and Z-axis by resolutions set in advance.

A pulser/receiver circuit 111 transmits a drive pulse signal to the ultrasonic probe 108 and receives a reflection echo signal from the ultrasonic probe 108. An analog peak detector 112 extracts the reflection echo signal relating to a desired inspection surface from the reflection echo signal received through a gate circuit and holds the peak value. An A/D conversion circuit 113 converts the analog peak values of the reflection echo signal to digital values while linking them with the trigger signals output from the encoders 110. A computer 114 is comprised of a CPU 115, keyboard 116, and main memory 117. The computer 114 controls the motor controller 109. Further, the computer 114 stores the digital peak values of the reflection echo signal in the main memory 117 through a data bus 118 and further displays the peak values on a monitor 119 in accordance with the planar coordinates. The data stored in the main memory 117 is used for various types of data processing. In addition, the pulser/receiver circuit 111 is similarly connected to an oscilloscope 120.

Figure 3:
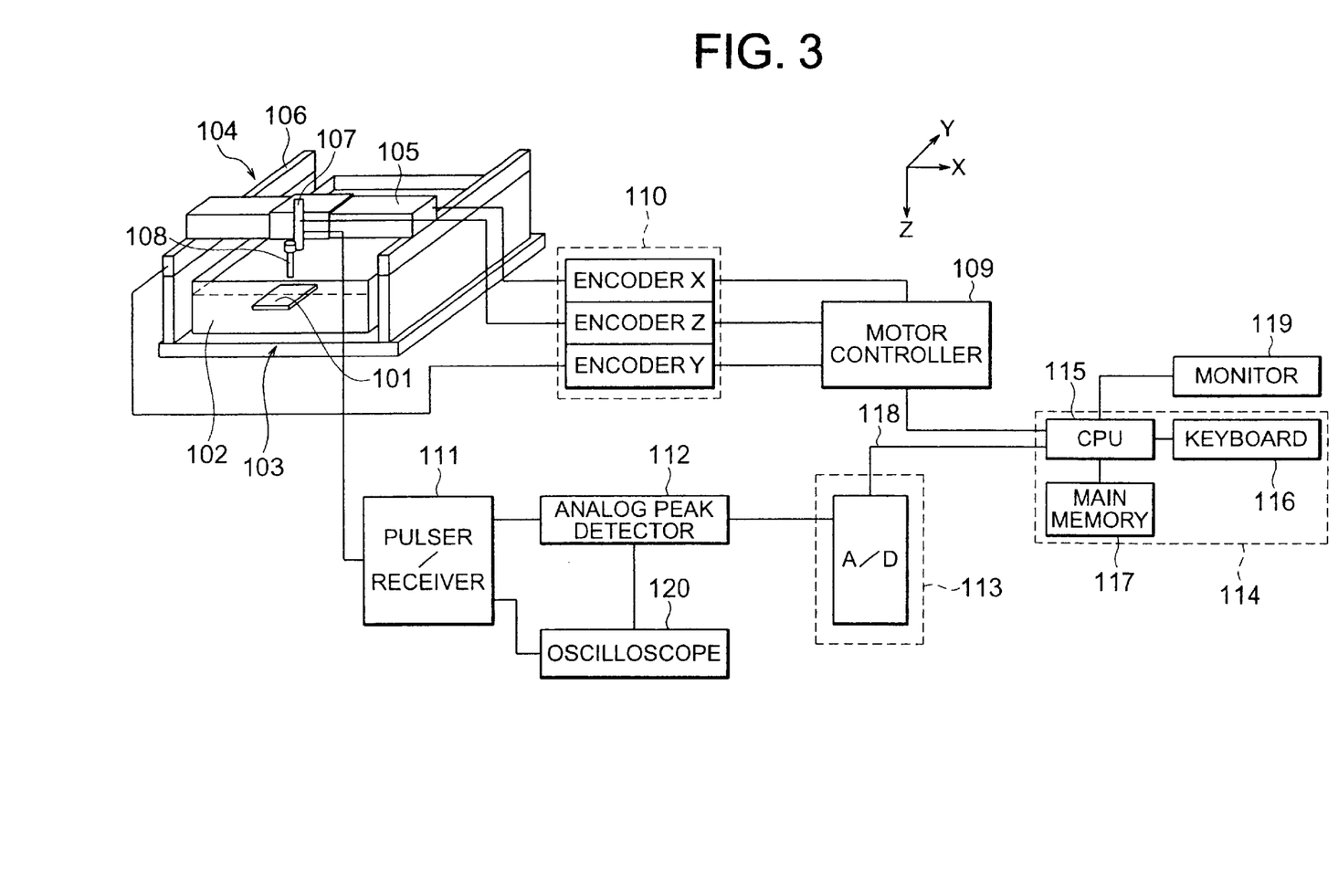
FIG. 3 is a block diagram of a conventional analog type ultrasonic inspection apparatus.

In the ultrasonic inspection apparatus shown in FIG. 3, the X-axis scanner 105 and the Y-axis scanner 106 scan planarly, while the ultrasonic probe 108 transmits an ultrasonic pulse toward the sample 101 based on the drive pulse signal given from the pulser/receiver circuit 111. The ultrasonic probe 108 receives the reflection echo signal returned from the sample 101. Using the received reflection echo signal, the analog peak detector 112 holds the peak values of the reflection echo signal near the desired inspection surface. The A/D conversion circuit 113 uses position trigger signals output from the encoders 110 to sample the data. Next, the computer 114 obtains the data, then displays an image based on the obtained signal on the monitor 119. In this way, a picture of the desired inspection surface in the sample 101 is obtained.

Figure 2A:
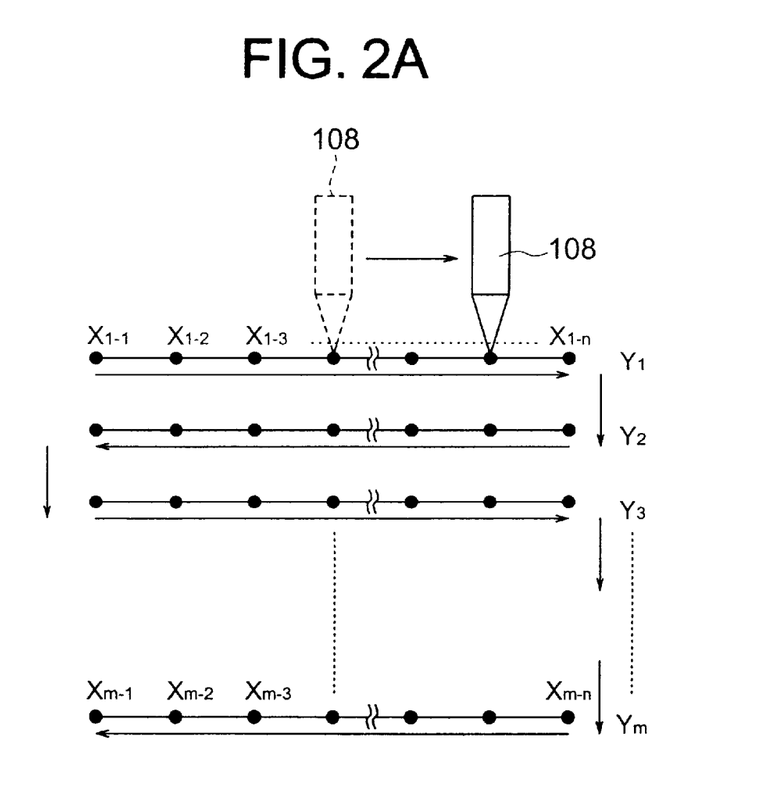
FIG. 2A is a schematic view of a two-dimensional scan of an X-axis scanner and Y-axis scanner and the sampling positions of digital waveform data at that time and shows the case of a two-directional scan.
Figure 2B:
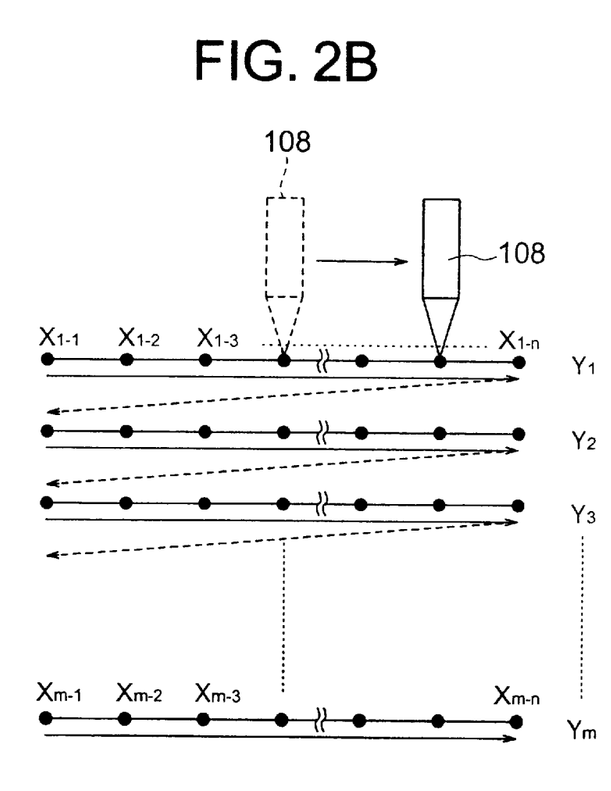
FIG. 2B is a schematic view of a two-dimensional scan of an X-axis scanner and Y-axis scanner and the sampling positions of digital waveform data at that time and shows the case of a one-directional scan.

There are two methods as shown in FIG. 2A and FIG. 2B for the X-axis and Y-axis planar scan by the X-axis scanner 105 and Y-axis scanner.

The method of measurement shown in FIG. 2A includes the step of having the A/D conversion circuit 113 use the position trigger signals output from the encoders 110 during a two-directional scan to sample data and the step of having the computer 114 display an image of the inspection surface echo signal obtained on the monitor 119. In this way, a picture of the desired inspection surface of the sample 101 is obtained on the monitor 119. This measurement method requires that before the feed scan in the Y-direction by the Y-axis scanner 106 is completed and the return scan of the X-direction by the X-axis scanner 105 is started, the transfer of data from the A/D conversion circuit 113 to the computer 114 be completed and the A/D conversion circuit 113 can sample the data during the return scan.

The method of measurement shown in FIG. 2B includes the step of having the A/D conversion circuit 113 use the position trigger signals output from the encoders 110 to sample data during the scan in the same direction at all times for the X-direction, and the step of having the computer 114 display an image based on the obtained inspection surface echo signal on the monitor 119. In this way, a picture of the desired inspection surface of the sample 101 is obtained on the monitor 119. This measurement method makes it possible to simultaneously perform a feed scan in the Y-direction by the Y-axis scanner 106 and return scan in the X-direction by the X-axis scanner 105. Further, it requires that, before the start of the next X-axis outgoing scan, the transfer of the data from the A/D conversion circuit 113 to the computer 114 be completed and the A/D conversion circuit 113 can sample data at the time of the next outgoing scan.

The number of the two-directional scans in the X-direction in the scan method of FIG. 2A is half that of the number in the scan method of FIG. 2B. Accordingly, in general, it is known that the scan time in FIG. 2A is shorter than the scan time in FIG. 2B.

As explained above, the analog type ultrasonic inspection apparatus shown in FIG. 3 can extract the peak values of a reflection echo signal of a desired inspection surface and produce a picture of the peak values. This ultrasonic inspection apparatus, however, requires several analog peak detectors when trying to simultaneously obtain peak values of reflection echo signals of several inspection surfaces. Further, when the ultrasonic inspection apparatus has several analog peak detectors, the problems of variations in the circuit characteristics among the detectors and the detection gate technology for reliably separating the echoes arise.

To solve these problems, a digital type ultrasonic inspection apparatus has been proposed. This digital type ultrasonic inspection apparatus uses a high speed A/D converter to convert the reflection echo signals to digital data and performs the gating and peak detection of the reflection echo signals at the desired positions digitally to instantaneously obtain information of several inspection surfaces.

Figure 4:
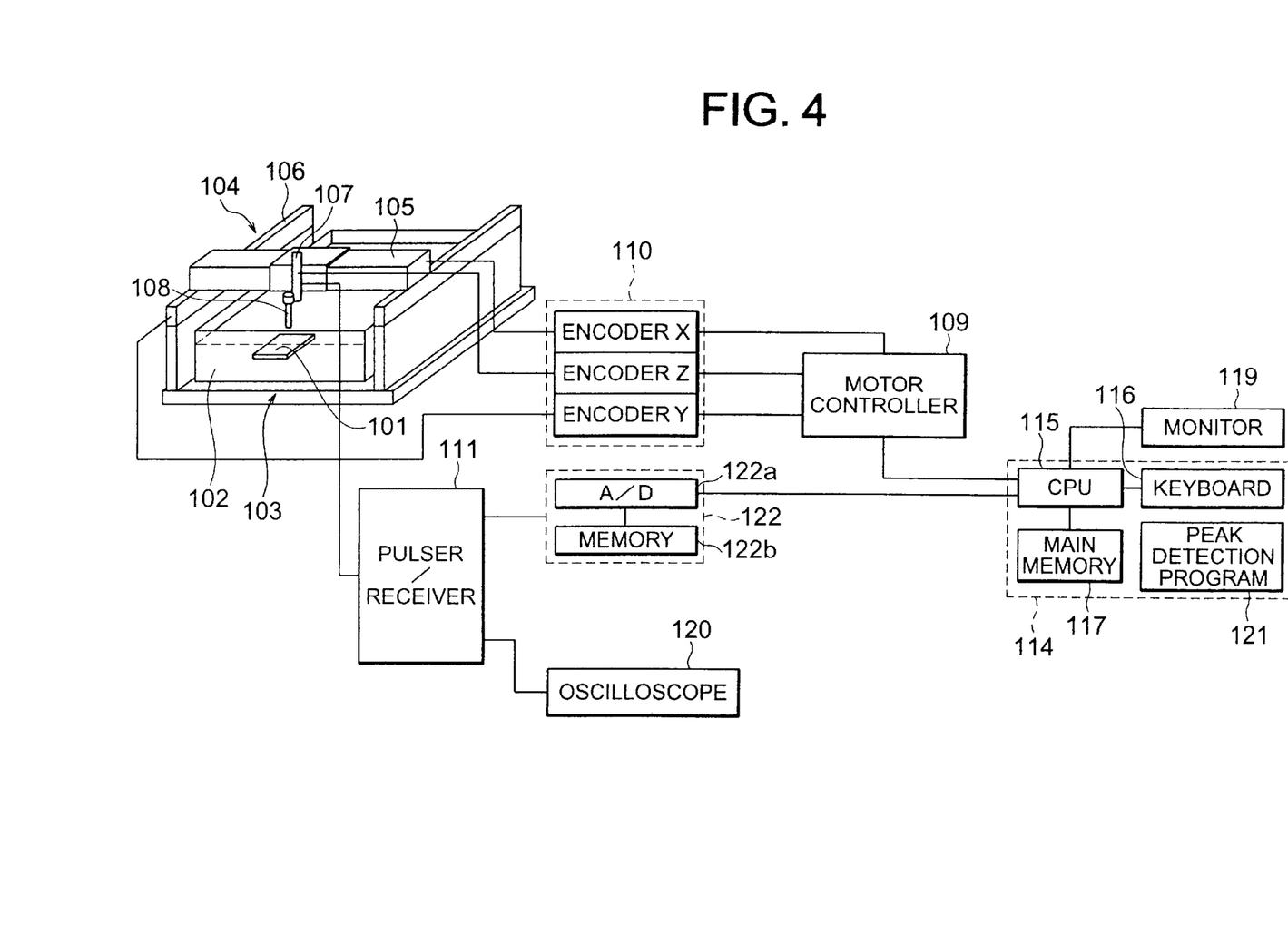
FIG. 4 is a block diagram of a conventional digital type ultrasonic inspection apparatus.

FIG. 4 shows an example of the digital type ultrasonic inspection apparatus. In FIG. 4, components in common with those of the analog type ultrasonic inspection apparatus explained above are assigned the same reference numerals for convenience in explanation. The digital type ultrasonic inspection apparatus has a peak detection program 121 within the memory of the computer 114 instead of the analog peak detector 112 of the analog type ultrasonic inspection apparatus. Further, instead of the A/D conversion circuit 113, an A/D converter 122 is provided. The A/D converter 122 is comprised of an A/D conversion circuit 122a and a memory 122b.

In the digital type ultrasonic inspection apparatus shown in FIG. 4, the A/D converter 122 samples the waveform data of several hundred to several thousand of points from the surface to the bottom of the sample 101 for each position trigger signal output from the encoders 110. The large number of waveform data sampled is stored in the memory 122b. The computer 114 performs the gating of the waveforms and the detection of the peak values of the desired inspection surface for the waveform data stored in the main memory 117 by the peak detection program 121. And it displays the digital peak values of the reflection echo signal of the desired inspection surface on the monitor 119. Due to this, a picture of an inspection surface in the sample 101 is obtained. The above-mentioned two planar scan measurement methods of FIG. 2A and FIG. 2B can be similarly used in the digital type ultrasonic inspection apparatus as well.

As explained above, in both the analog type and digital type ultrasonic inspection apparatus, the individual sampled data obtained based on the position trigger signals output from the encoders 110 are arranged as shown in FIGS. 2A and 2B. In particular, in the analog type ultrasonic inspection apparatus, peak detection values in the gates at the positions $X_{1-1}, X_{1-2}, \ldots, X_{m-n}$ corresponding to the arrangement of the sampling positions, that is, the digital peak values, are sampled at those positions. The digital peak values are for example 1 byte of peak value data.

On the other hand, in the digital type ultrasonic inspection apparatus, since a program is used for peak detection, digital data of waveforms at the positions $X_{1-1}, X_{1-2}, \ldots, X_{m-n}$ corresponding to the arrangement of the sampling positions, for example, the waveform data of several hundred to several thousands of points (for example, unit: bytes), are sampled at those positions. Therefore, the number of points of data sampled in the digital type ultrasonic inspection apparatus becomes several hundred to several thousand times the amount of data sampled in the analog type ultrasonic inspection apparatus. Therefore, when configuring the digital type ultrasonic inspection apparatus, in particular in the case of FIG. 2A, it is required that before the feed scan in the Y-direction and the return scan in the X-direction are started, the transfer of data from the memory 122b of the A/D converter 122 to the computer 114 be completed and the A/D converter 122 can sample data at the time of the return scan. Therefore, the digital type ultrasonic inspection apparatus requires technology for a high-speed data transfer system.

In the above-explanation, the problems in the planar scan by the ultrasonic inspection apparatus were explained. However, the problems are not limited to the planar scan. The above problems similarly occur in spiral rotational scans or inclined scans by the ultrasonic inspection apparatus.

SUMMARY OF THE INVENTION

An object of the present invention is to provide an ultrasonic inspection apparatus of a digital type realizing a system of high speed data transfer not affecting data sampling at the time of scanning in, for example, a two-directional type planar scan, enabling transfer of a high volume of data, and thereby reducing the dead time at the time of scanner scans to zero to enable measurement by high speed scans.

The ultrasonic inspection apparatus according to the present invention is configured as follows to achieve the above object.

The first ultrasonic inspection apparatus of the invention scans a sample by an ultrasonic probe by scanners of at least two axes, transmits an ultrasonic wave from the ultrasonic probe toward the sample, and receives the reflection echo signal returning from the sample. The waveforms received at the A/D converter are converted to digital waveform data with each sampling position trigger output from the encoders of the scanners. The digital waveform data output from the A/D converter is transferred to the computer where it is processed in various ways. The ultrasonic inspection apparatus is further provided with at least two data memories controlled in operating states by a scan state monitoring signal setting a unit measurement range in accordance with the operating state in advance and changing with each change of the unit measurement range when continuously scanning a plurality of unit measurement ranges and a memory controller for receiving as input a trigger signal based on the detection values of the above encoders, changing the scan state monitoring signal with each change of the unit measurement range, and outputting the scan state monitoring signal to the at least two data memories. In the above configuration, the memory controller controls the operation states of the at least two data memories based on the scan state monitoring signal, that is, performs control to alternately write digital waveform data from the A/D converter to a data memory, read digital waveform data from a data memory by the computer, and transfer data to the memory of the computer.

The second ultrasonic inspection apparatus that has the configuration of the above-mentioned first apparatus, is preferably configured such that the memory controller is provided with a counter for counting the number of the position triggers determined by encoders corresponding to the sampling position coordinates when scanning a unit measurement range, a comparator-register for comparing the count of the counter and the number of position triggers in the set unit measurement range and outputting a signal for changing the scan state monitoring signal each time the results of the comparison are a match, and a memory-control-circuit for outputting a scan state monitoring signal for controlling the operating states of the at least two data memories based on the signal given from this comparator-register.

The third ultrasonic inspection apparatus that has the configurations of the above apparatuses, is preferably configured such that the at least two data memories are comprised of a first data memory and second data memory and the memory controller outputs a scan state monitoring signal of a first state and second state. When the scan state monitoring signal is the first state, it is possible to write data into the first data memory and read out data from the second data memory. The digital waveform data outputted from the A/D converter is continuously written into the first data memory, and simultaneously the digital waveform data is continuously read out from the second data memory in the computer. When the scan state monitoring signal is the second state, it is possible to read out data from the first data memory and write data into the second data memory. The digital waveform data obtained by sampling operation of the A/D converter is continuously written into the second data memory, and simultaneously the digital waveform data is continuously read out from the first data memory.

The fourth ultrasonic inspection apparatus that has the configuration of the above apparatuses, is preferably configured such that the second data memory write-enabled by the change of the scan state monitoring signal from the first state to the second state is continuously written with data from the digital waveform data after the final digital waveform data in the first data memory write-enabled when the scan state monitoring signal is the first state so as to preserve the continuity of data stored between the first data memory and second data memory.

The fifth ultrasonic inspection apparatus that has the configuration of the above apparatuses, is preferably configured such that the computer is provided with means for storing the digital waveform data read out from the at least two data memories at addresses corresponding to the sampling positions on the memory of the computer. Due to this means, the data is transferred continuously from the data memories to addresses on the memory of the computer by direct memory access (DMA).

In the configuration of the ultrasonic inspection apparatus according to the present invention, the waveform data obtained by the measurement is processed digitally. The reflection echo returned from the inspected object or the sample is received by an ultrasonic probe and converted into an electric analog signal. The analog signal is converted (digitalized) to digital waveform data at several hundred to several thousand of points of the waveform from the sample surface to bottom using a high speed A/D converter for each position trigger corresponding to a sampling position output from the encoders of the scanners.

In the digital type ultrasonic inspection apparatus according to the present invention, the converted digital waveform data is temporarily stored in the data memory section, then transferred to the memory of the computer for storage. The data memory section is comprised of at least two data memories. In the measurement scan, since a large amount of digital waveform data of several hundred to several thousand of points is prepared and stored, a unit measurement range corresponding to a scan operation is set and a data memory for storing the waveform data is selected and temporarily stored-in based on a switching operation by the memory controller. Due to this, it is possible to continuously perform measurement scans, sample waveform data by the A/D converter, and transfer digital waveform data from the data memories to the computer side memory by the computer without stopping. Therefore, it is possible to eliminate loss time due to transfer of data.

When the sample scan at the ultrasonic inspection apparatus according to the present invention is a planar scan for a representative XY plane, a two-dimensional scan by the X-axis scanner and Y-axis scanner is performed. During the two-dimensional scan, it is possible to continuously sample waveform data through the A/D converter and transfer digital waveform data from the data memories to the computer side memory by the computer without stopping. In this case, after the first line scan operation in the X-direction by the X-axis scanner and the feed operation in the Y-direction by the Y-axis scanner after that, without waiting for the end of the transfer of the first line digital waveform data, a second line X-direction scan and the later Y-direction feed become possible, so it is possible to eliminate loss time due to transfer of data.

In the case of a planar scan of the XY plane, the above-mentioned "unit range of measurement" is, for example, one line in the X-direction. In this case, the odd numbered one-line scan portions become odd-numbered measurement ranges, while the even-numbered one-line scan portions become even-numbered one-line scan portions. The changes in the two signal shapes of a scan state monitoring signal arise in accordance with changes from the even-numbered measurement range from the odd-numbered measurement range or changes from the odd-numbered measurement range from the even-numbered measurement range.

BRIEF DESCRIPTION OF THE DRAWINGS

These and other objects and features of the present invention will become clearer from the following description of the preferred embodiments given with reference to the attached drawings, wherein.

DESCRIPTION OF THE PREFERRED EMBODIMENTS

Preferred embodiments of the present invention will be described in detail below while referring to the attached figures. A representative embodiment of the present invention will be explained first with reference to FIG. 1 and FIG. 2A. This embodiment shows the configuration of a digital type ultrasonic inspection apparatus. In this apparatus, the X-axis scanner and Y-axis scanner perform a two-directional type two-dimensional scan, that is, a planar scan. That is, this embodiment explains an example of measurement by scanning a plane (XY plane) defined by the X-axis and Y-axis. Components shown in FIG. 1 being as same as the components explained in FIG. 3 and FIG. 4 above are assigned the same reference numerals.

Figure 1:
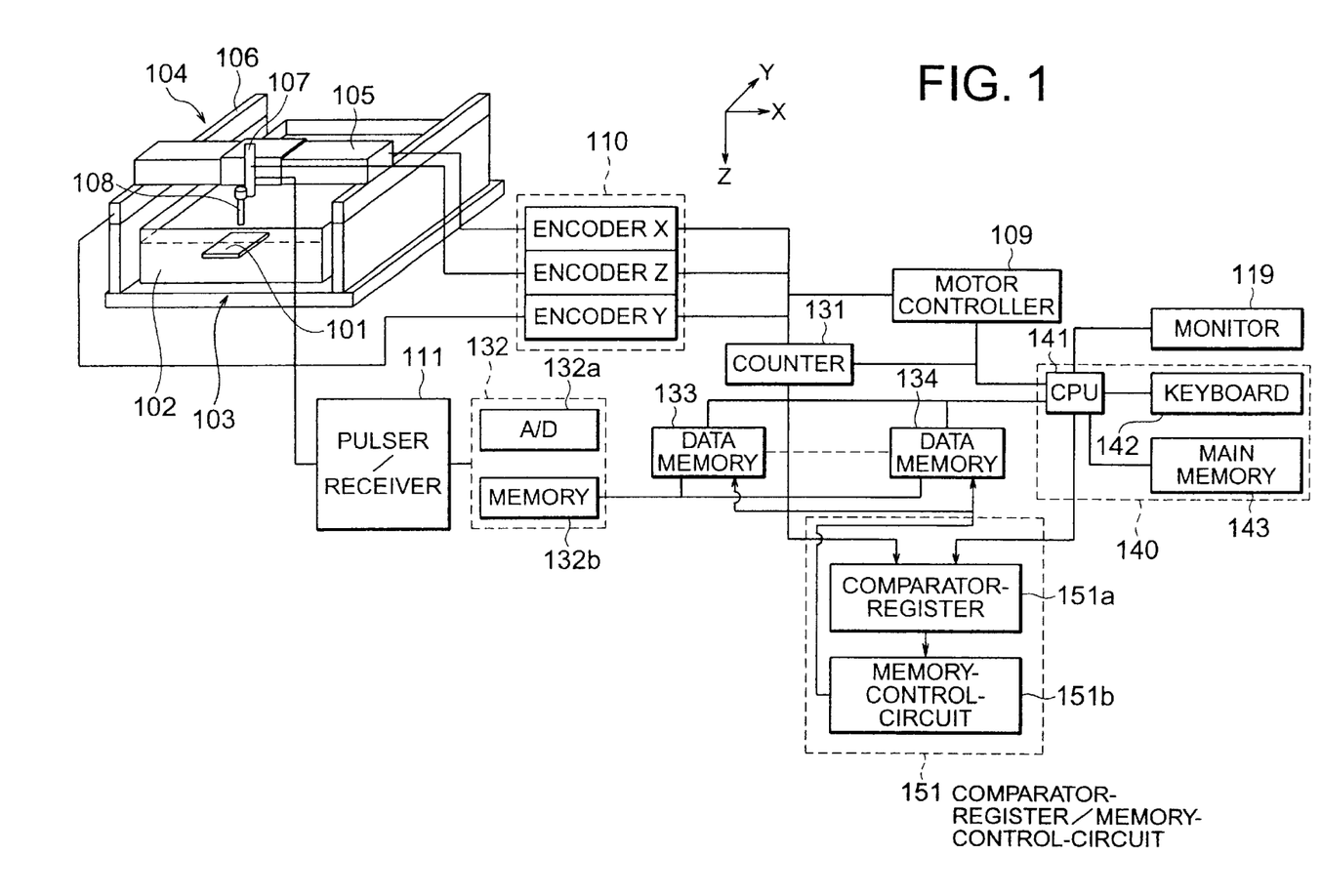
FIG. 1 is a block diagram of a representative embodiment of an ultrasonic inspection apparatus according to the present invention.

The configuration will be explained with reference to FIG. 1. A sample 101 is placed in the water of a water tank 102. A scanner 104 is placed at the water tank 102. The water tank 102 is placed on a measurement stage 103. The scanner 104 is attached to the measurement stage 103. The scanner 104 is comprised of an X-axis scanner 105 for performing a scan in the X-direction, a Y-axis scanner 106 for performing a scan in the Y-direction, and Z-axis scanner 107 for performing a scan in the Z-direction. The Z-axis scanner 107 is provided at its bottom with an ultrasonic probe (ultrasonic sensor) 108. The tip of the ultrasonic probe 108 faces the sample 101. The scan X-axis, Y-axis and Z-axis of the scanner 104 are perpendicular to each other. The operations of the X-axis scanner 105, Y-axis scanner 106, and Z-axis scanner 107 of the scanner 104 are controlled by a motor controller 109. Based on the control of the motor controller 109, the scanner 104 performs scan operations along the three axes, which are mutually independent and perpendicular. The motors of the three axes have encoders 110 respectively. The encoders 110 for the X-axis, Y-axis and Z-axis output signals of position triggers corresponding to the positional coordinates on the three axes. The encoders 110 are provided with a counter 131. A pulser/receiver circuit 111 transmits an ultrasonic wave pulse use drive signal to the ultrasonic probe 108 and receives a reflection echo signal from the ultrasonic probe 108. The received reflection echo signal is input to an A/D converter 132. The A/D converter 132 is comprised of an A/D conversion circuit 132a and a memory 132b. The memory 132b of the A/D converter 132 is further provided with at least two data memories 133 and 134. The number of the data memories is preferably two, but is not limited to two. The data memories 133 and 134 store the sampled and digitized waveform data. The storage capacities of the data memories 133 and 134 are determined in accordance with the unit measurement ranges as discussed later (for example, measurement range of one scan line in X-direction).

The computer 140 is provided with a CPU 141, keyboard 142, and main memory 143. The computer 140 is further provided with a monitor 144. The computer 140 is additionally provided with a comparator-register/memory-control-circuit 151. The comparator-register/memory-control-circuit 151 receives as input the output signal from the counter 131 (signal relating to count) and controls the drive states of the data memories 133 and 134 based on the scan state monitoring signal output to the data memories 133 and 134. It also controls the transfer of the stored data to the CPU 141. The internal memory of the computer 140 is provided with a peak detection program. The peak detection program is executed by the CPU 141 and thereby forms a peak detector. The computer 140 controls the operations of the motor controller 109, counter 131, and comparator-register/memory-control-circuit 151. In addition, the computer 140 gives data relating to the number of position triggers in a preset unit measurement range to the comparator-register/memory-control-circuit 151. Further, the counter 131 counts the number of position triggers determined by the encoders 110 corresponding to the sampling position coordinates at the time of scanning the unit measurement range.

The comparator-register/memory-control-circuit 151 compares the count of the counter 131 and the number of the position triggers in the set unit measurement range. The comparator-register/memory-control-circuit 151 outputs the above scan state monitoring signal to the two data memories 133 and 134 each time the results of comparison of the two are a match. The scan state monitoring signal, as one example, uses for example one multiple of one scan line (in general a whole number multiple) as the "unit measurement range" and indicates the scan state of odd-numbered measurement ranges (in general measurement ranges belonging to a first group) or even-numbered measurement ranges (in general measurement ranges belonging to a second group) when continuously scanning a plurality of measurement ranges.

The comparator-register/memory-control-circuit 151 more particularly is comprised of a comparator-register 151a and a memory-control-circuit 151b. The comparator-register 151a compares the count of the counter 131 and the number of position triggers in the set unit measurement range and provides a coincidence signal to the memory-control-circuit 151b when the results of comparison are a match. The memory-control-circuit 151b, based on the coincidence signal from the comparator-register 151A, considers the operating states of the two data memories 133 and 134 and outputs the scan state monitoring signal determining the operating states of the two data memories 133 and 134 to the data memories 133 and 134. The operating states of the two data memories 133 and 134 are switched by the scan state monitoring signal. The above counter, comparator-register, and memory-control-circuit form a memory control means for controlling the operating states of the data memories 133 and 134.

Next, the sequence at the time of operation of the digital type ultrasonic inspection apparatus having the above configuration will be explained. In this embodiment, the above "unit measurement range" is as one example made one scan line in the X-direction.

The ultrasonic probe 108 transmits a pulse-like ultrasonic wave toward the inside interface of the sample 101 (XY plane inside sample) and receives a reflection echo from the sample 101 while moving from $X_{1-1}$ to $X_{1-n}$ along with the scan in the X-direction (scan from left to right). During this time, the encoder 110 in question outputs trigger signals a t the preset sampling positions $X_{1-1}, X_{1-2}, X_{1-3}, \ldots, X_{1-n}$. At each position trigger, the A/D converter 132 samples the waveform data for example from the surface to the bottom of the sample (for example, 1000 points (unit: bytes) of data). The total number of points of the waveform data sampled at the time when one line finishes being scanned from $X_{1-1}$ to $X_{1-n}$ (n=number of position triggers, for example, n=1000) becomes (the number of waveform data ×n=1000×1000)=1 Megabyte. This is 1000 times greater than the number of data when the analog type ultrasonic inspection apparatus samples peak values obtained by peak value detection at an above sampling position under the same conditions.

Linked with the scan of the first line and the sampling of the waveform data, the comparator-register/memory-control-circuit 151 is in the middle of measuring the first line waveform data, so outputs a write enable signal to the data memory 133 as the scan state monitoring signal to permit writing of digital waveform data from the A/D converter 132 and simultaneously outputs a read enable signal to the data memory 134 to permit reading of data from the computer 140 and transfer of data to the main memory 143. The A/D converter 132 writes the converted digital waveform data sampled continuously to the data memory 133. At this time, since it is in the middle of measurement of the first line, the data memory 134 does not store the desired waveform data, so the computer 140 does not read out the digital waveform data from the data memory 134.

Next, the end of the feed operation of the pitch ($Y_1$) corresponding to the distance between $X_{1-1}$ and $X_{1-2}$ by the Y-axis scanner 106 of the scanner 104 is awaited, then the X-axis scanner 105 performs a return scan (scan from right to left) while passing through the sampling positions of $X_{2-n}, X_{2-(n-1)}, X_{2-(n-2)}, \ldots, X_{2-1}$ from $X_{1-n}$ to the direction of $X_{1-1}$.

At this time, assuming that the Y-axis scanner 106 is in the middle of measuring the X-direction second line waveform data from the point of time of the start of the feed scan of the pitch $Y_1$, the comparator-register/memory-control-circuit 151 outputs a write enable signal to the data memory 134 as the scan state monitoring signal to permit writing of digital waveform data from the A/D converter 132, and simultaneously outputs a read enable signal to the data memory 133 to permit reading of data by the computer 140 and transfer of data to the main memory 143. The A/D converter 132 writes the second line digital waveform data sampled at the sampling positions passed through in the order of $X_{2-n}$, $X_{2-(n-1)}, X_{2-(n-2)}, \ldots, X_{2-1}$ continuously in the data memory 134. Simultaneously, the computer 140 continuously reads out the first line waveform data from the data memory 133. To increase the speed of the data transfer, the computer 140 has a functional part for arranging digital waveform data by DMA (Direct Memory Access) transfer at addresses on the main memory 143.

Next, after the feed of the pitch $Y_2$ by the Y-axis scanner 106 is ended, the X-axis scanner 105 scans the third line while passing through the sampling positions of $X_{3-1}$, $X_{3-2}, \ldots, X_{3-n}$ in the same way as from the above $X_{1-1}$ to the $X_{1-n}$ direction (left side to right side). Assuming that the Y-axis scanner 106 is in the middle of measuring the third line waveform data from the point of time of the start of the feed scan of the pitch $Y_2$, the comparator-register/memory-control-circuit 151 outputs a write enable signal to the data memory 133 as the scan state monitoring signal to permit writing of data from the A/D converter 132, and simultaneously outputs a read enable signal to the data memory 134 to permit reading of data by the computer 140. The A/D converter 132 writes the third line digital waveform data sampled at the sampling positions passed through in the order of $X_{3-1}, X_{3-2}, \ldots, X_{3-n}$ again continuously in the data memory 133. Simultaneously, the computer 140 continuously reads out the second line waveform data from the data memory 134 and arranges the digital waveform data by the DMA transfer at the second line address in the main memory 143 of the computer 140.

As explained above, in the digital type ultrasonic inspection apparatus according to the present embodiment, the data memories 133 and 134 can alternately be read out from and written into linked with the scans of the X-axis and Y-axis odd-numbered lines and even-numbered lines. During the measurement, the X-axis scanner 105 and the Y-axis scanner 106 are never stopped by fetching of digital waveform data. In this way, it is possible to write and read out digital waveform data continuously without interruption. The above-mentioned sequence is repeated until the final line $X_{m-1}, X_{m-2}, X_{m-3}, \ldots, X_{m-n}$ digital waveform data finishes being arranged at the n—th line address in the main memory 143 of the computer 140. High speed data transfer can be realized for transfer of the digital waveform data.

The storage and transfer of digital waveform data according to the above embodiment can also be applied to the scan method of FIG. 2B. The storage capacities of the data memories 133 and 134 are determined by the amount of digital waveform data determined by the unit measurement range. Further, the unit measurement range does not have to be limited to one scan line. In storing the data according to the acquisition of the digital waveform data and transferring it to the main memory of the computer, this can be set in any way so long as it is possible to perform measurement without stopping the scan operation.

In the above-mentioned embodiments, the CPU 141 executes the peak detection program, but it is also possible to have the processing for peak detection be performed by another CPU or digital signal processor (DSP) to lighten the load on the CPU 141.

Further, in the above-mentioned embodiments, the number of position triggers for sampling waveform data is counted and the memories are controlled by switching the scan state monitoring signal, but it is also possible to use other trigger signals than the above position triggers such as triggers linked with the scan in the Y-direction.

In the above-mentioned embodiments, the explanation was given of the example of the planar scan for the XY plane, but the scan is not limited to the planar scan. The present invention can also be applied to a spiral rotational scan or an inclined scan in three dimensions etc. Further, even in the planar scan, the present invention can be applied to a scan in the XZ plane or YZ plane. Further, it is possible to freely set any "unit measurement range", not only for each scan line, by linking it with a scan operation in advance.

The present invention is the ultrasonic inspection apparatus processing the waveform data obtained by measurement digitally, where during scanning by scanners of at least two axes such as the X-axis scanner and Y-axis scanner, the writing of digital waveform data sampled by the A/D converter into the data memory, the reading of digital waveform data by the computer, and the transfer of data to the main memory of the computer are performed switched between at least two data memories. Therefore, it is possible to continuously perform a repetition of a scan of a first scanner in a first unit measurement range, feed in another direction later, scan of the first scanner in a second unit measurement range, and feed in another direction later without interruption. Further, it is possible to continue the scans from one to the next without waiting for the end of transfer of digital waveform data and possible to eliminate the wait time due to the scanners and perform ultrasonic inspections at a high speed.

The present disclosure relates to subject matter contained in Japanese Patent Application No. 2002-65909, filed on Mar. 11, 2000, the disclosure of which is expressly incorporated herein by reference in its entirety.

What is claimed is:

1. An ultrasonic inspection apparatus which scans a sample with an ultrasonic probe by scanners of at least two axes, transmits an ultrasonic wave from said ultrasonic probe toward said sample, receives a reflection echo signal returning from said sample, converts waveforms received by an A/D converting means to digital waveform data with each sampling position trigger output from encoders of said scanners, transfers said digital waveform data from said A/D converting means to a computer, and performs various types of processing, comprised of:

at least two data memories controlled in operating state by a scan state monitoring signal setting a unit measurement range in accordance with the operating state in advance and changing with each change of the unit measurement range when continuously scanning a plurality of unit measurement ranges; and a memory control means for receiving as input a trigger signal based on the detection values of the said encoders, changing said scan state monitoring signal with each change of said unit measurement range, and outputting the scan state monitoring signal to said at least two data memories;

wherein said memory controller controls the operating states of said at least two data memories based on said scan state monitoring signal so as to alternately write said digital waveform data from said A/D converting means to said data memory, and read said digital waveform data from said data memory by said computer and transfer data to the memory of said computer.

2. An ultrasonic inspection apparatus as set forth in claim 1, wherein said memory control means is comprised of;

a counter for counting the number of said position triggers determined by said encoders corresponding to the sampling position coordinates when scanning said unit measurement range, a comparator-register for comparing the count of said counter and the number of position triggers in said set unit measurement range and outputting a signal for changing said scan state monitoring signal each time the results of the comparison are a match, and a memory-control-circuit for outputting said scan state monitoring signal for controlling the operating states of said at least two data memories based on said signal given from said comparator-register.

3. An ultrasonic inspection apparatus as set forth in claim 1, wherein said at least two data memories are comprised of a first data memory and second data memory, said memory control means outputs a scan state monitoring signal of a first state and second state, when said scan state monitoring signal is the first state, said first data memory can be written in and said second data memory can read from, the digital waveform data sampled by said A/D converting means is continuously written into said first data memory, and simultaneously digital waveform data is continuously read out by said computer from said second data memory, and when said scan state monitoring signal is the second state, said first data memory can be read from and said second data memory can written into, the digital waveform data sampled by said A/D converting means is continuously written into said second data memory, and simultaneously digital waveform data is continuously read out by said computer from said first data memory.

4. An ultrasonic inspection apparatus as set forth in claim 3, wherein said second data memory write-enabled by the change of said scan state monitoring signal from the first state to the second state is continuously written with data from the digital waveform data after the final digital waveform data in said first data memory write-enabled when said scan state monitoring signal is the first state so as to preserve the continuity of data stored between said first data memory and said second data memory.

5. An ultrasonic inspection apparatus as set forth in claim 1, wherein said computer is provided with means for storing said digital waveform data read out from said at least two data memories at addresses corresponding to sampling positions on a memory of said computer and data is transferred continuously from said data memories to addresses on the memory of said computer by DMA.

* * * * *